United States Patent [19]

Cukier

[11] Patent Number: 4,910,803
[45] Date of Patent: Mar. 27, 1990

[54] APPAREL HAVING A BREACH INDICATOR

[76] Inventor: Daniel S. Cukier, 450 Knollwood Rd., Ridgewood, N.J. 07450

[21] Appl. No.: 269,724

[22] Filed: Nov. 10, 1988

Related U.S. Application Data

[62] Division of Ser. No. 127,440, Dec. 2, 1987.

[51] Int. Cl.$^4$ .................... A41D 19/00; G01N 21/31
[52] U.S. Cl. ...................................... 2/168; 128/638; 128/2; 128/2 G; 128/844; 128/918; 436/2; 436/3; 436/66; 436/164; 422/58
[58] Field of Search ............... 428/916; 604/361, 362; 128/132 R, 744, 284, 285; 2/161 R, 164, 167, 168, DIG. 7; 436/164, 169, 183, 63, 66, 2, 3; 422/58

[56] References Cited

U.S. PATENT DOCUMENTS

| | | | |
|---|---|---|---|
| 2,577,345 | 8/1950 | McEwen | 128/294 |
| 3,097,636 | 7/1963 | Haynes et al. | 2/168 |
| 3,633,216 | 1/1972 | Schonholtz et al. | 128/638 |
| 3,672,351 | 6/1972 | Ubersax et al. | 128/2 G |
| 3,675,654 | 7/1972 | Baker et al. | 128/287 |
| 3,731,685 | 5/1973 | Eidus | 128/284 |
| 3,794,024 | 2/1974 | Kokx et al. | 128/285 |
| 4,432,357 | 2/1984 | Pomeranz | 128/79 |
| 4,446,860 | 5/1984 | Gutnick | 128/132 |
| 4,473,079 | 9/1984 | Jasper et al. | 128/638 |
| 4,498,466 | 2/1985 | Pomeranz | 128/79 |
| 4,559,949 | 12/1985 | Levine | 128/638 |
| 4,564,006 | 1/1986 | Pomeranz | 128/79 |

FOREIGN PATENT DOCUMENTS 1144354 4/1983 Canada .

*Primary Examiner*—Barry S. Richman
*Assistant Examiner*—Lyle Alfaddary-Alexander
*Attorney, Agent, or Firm*—Lerner, David, Littenberg, Krumholz & Mentlik

[57] ABSTRACT

Disclosed is a composite material adaptable to form bodily fluid protection apparel that can alert a wearer that a breach in the apparel has occurred. The apparel comprises a first layer impervious to bodily fluid and a second layer supporting the first layer. The second layer comprises a bodily fluid detection means indicating the presence of bodily fluid. A variety of apparel, including gloves and masks, can be formed. Any one of a number of bodily fluids, including blood, saliva, and semen, can be detected by the detection means.

30 Claims, 1 Drawing Sheet

APPAREL HAVING A BREACH INDICATOR

This is a division, of application Ser. No. 127,440, filed Dec. 2, 1987.

FIELD OF THE INVENTION

This invention pertains to the field of protective apparel. Particularly, this invention relates to protective apparel that comprises an indicator or detector alerting the wearer that the protective apparel is breached, thereby no longer serving a protective function. More particularly, this invention pertains to a glove designed to protect the wearer from exposure to bodily fluids such as blood or saliva.

BACKGROUND OF THE INVENTION

Modern medicine has provided a heretofore unprecedented level of freedom from the ravages of infectious disease. Beginning in the midnineteenth century with the development of antiseptics, extending through the development of sulfa drugs in the early twentieth century, and continuing with the advent of penicillin and other antibiotics in the midtwentieth century, modern medicine has succeeded in attaining a very high level of prevention and cure of infectious diseases. Moreover, the art of vaccine development has reached a level of sophistication such that many infectious diseases, such as smallpox, have effectively been eradicated from many countries including the United States.

Nonetheless, certain highly contagious diseases are still extant and are easily spread throughout the population. Common examples of such infectious afflictions are hepatitis, meningitis, syphilis, and gonorrhea. Because these diseases have long been known to medical science, mechanisms for dealing with patients suffering from such diseases have been developed that minimize the chance of persons becoming infected as a result of exposure to afflicted patients. Despite these mechanisms, contagion of these diseases is still a problem confronting medical workers and public health authorities. Modern science is also confronting new diseases, such as Legionnaires' disease and Acquired Immune Deficiency Syndrome (AIDS), for which no longstanding contagion mitigating mechanism is in place.

One way the spread of disease is reduced or minimized is by protecting a noninfected person from exposure to the etiologic agents of disease by means of a barrier. In the particular case of AIDS, great levels of concern and anxiety are associated with interaction between patients suffering from the disease or persons considered in a high-risk category, and others. Indeed, the concern of the entire population with respect to becoming infected with AIDS is so great that in some instances, children suffering from the disease have not been permitted in schools; medical workers, including physicians, have refused to treat or have expressed reluctance to treat AIDS patients; and other workers likely to come in contact with AIDS sufferers, such as emergency medical service personnel and law enforcement officers, are concerned that they may become infected with AIDS by virtue of their contact with an AIDS patient or carrier. In view of the fatal course of the AIDS infection, these groups of people, as well as others, are not only nervous about dealing with known AIDS sufferers but are also concerned about treating or coming into contact with any individual in the population because such an individual may be an undiagnosed AIDS sufferer, a carrier of the etiologic agent of AIDS, or an AIDS sufferer not showing outward clinical manifestations of the disease.

It is now believed that the etiologic cause of AIDS is a virus. The virus has been designated HIV (human immunodeficiency virus) formerly known as HTLV III. To spread, this viral agent must be transmitted from one person to another—for instance, by contact with the blood and perhaps other bodily fluids of an afflicted individual. In response to the threat of contagion associated with this mechanism of transmission, persons likely to come in contact with the HIV virus have begun routinely wearing or carrying protective apparel that reduces the chance that they will come in contact with the blood or bodily fluids of an AIDS afflicted individual. Indeed, the wearing of AIDS protective apparel is now strongly urged for many health care workers, and the Centers for Disease Control is drafting new guidelines in this regard.

Moreover, nonmedical personnel who may come in contact with AIDS patients or individuals from known high-risk AIDS groups now commonly carry protective gloves to serve as a barrier between themselves and the bodily fluids of AIDS patients or possible AIDS carriers. For example, the New York City Board of Education, at the urging of the City Health Commissioner, is distributing disposable gloves to all city schools in an effort to protect teachers and other employees from contracting AIDS. Such a policy is being carried out in many schools, hospitals, medical service departments, and research laboratories throughout the country.

There is a major problem with the use of bodily fluid protective or barrier apparel. The problem is that the wearer of the apparel cannot determine whether the apparel has been breached or otherwise circumvented unless such a breach or circumvention is noticeable to the wearer. This problem is particularly acute in the case of AIDS, other viral diseases such as hepatitis, and certain bacterial infections owing to the extraordinarily small size, even by microscopic standards, of the microbial etiologic agents of these diseases. There are literally billions of these disease-causing agents in even a microscopic droplet of blood or other bodily fluid. Consequently, an individual, even though wearing a form of barrier or protective apparel, may unwittingly be exposed to an infectious agent such as the AIDS virus because the wearer cannot detect the fact that he is in contact with a microscopic amount of bodily fluid or blood.

This problem is especially acute in the case of protective apparel worn by medical professionals. Such apparel, most especially surgical-type gloves, may have, for instance, microscopic holes or other non-noticeable breaches, e.g. caused by needles from syringes being used to withdraw blood from a patient. These breaches cannot be detected by a medical worker. Dentists face similar threats because small breaches in gloves worn by them may occur from their use of syringe needles, sharp dental instruments, or from contact with sharp teeth. Blood, saliva, or other bodily fluid from a patient suffering from a highly contagious disease such as AIDS can pass through such a breach in the protective apparel and, by going unnoticed by the wearer, expose the wearer to the disease. This is a serious problem because the wearer may be falsely confident that the protective apparel is an adequate barrier to contact with and spread of the disease.

The instant invention significantly allays the fears of medical workers and others concerned about exposure to AIDS or other infectious diseases by virtue of coming into contact with bodily fluids, most notably blood, of persons harboring disease-causing microbes. This is accomplished by incorporating into protective apparel a means for detection of blood or other bodily fluid. Detection occurs by triggering at least one chemical marker for a specific bodily fluid, indicating to the wearer the presence of the specific bodily fluid. It is currently preferred that the means of indicating the presence of bodily fluid to the wearer will be through the use of a color indicator such as a known dye or chromagen. Through the use of this invention, medical workers, teachers, police, and other persons will no longer fail to treat or otherwise interact with AIDS sufferers or with people apprehended as carrying a highly infectious agent. Still further and perhaps more importantly, it will give to these workers a high level of confidence that their chance of becoming infected by an infectious agent such as the AIDS virus is minimized. This confidence will result because this invention permits the user of the invention to easily discern whether he is in contact with a specific bodily fluid that may contain the etiologic agent of disease.

It is therefore an object of this invention to provide a piece of wearing apparel which, upon breach of the apparel, can indicate to the wearer the presence of such a breach by demonstrating that the wearer is in danger of coming or has come into contact with specific bodily fluids harboring a disease-causing agent.

SUMMARY OF THE INVENTION

This invention discloses a material that can be formed into protective apparel that can alert a person using the apparel or material that a specific bodily fluid has penetrated the material or apparel. The use of such material or apparel would be especially beneficial in dealing with individuals who are afflicted with highly contagious diseases or are carriers of such diseases. When used for this purpose, the instant invention provides a measure of safety and confidence to persons not afflicted with or carrying a highly contagious disease when such unafflicted persons deal with persons afflicted by the disease or carrying the disease.

A bodily fluid protection apparel for protecting at least a portion of a wearer's body is disclosed, which alerts the wearer that a breach in the apparel has occurred. The apparel comprises a first layer impervious to bodily fluid and a second layer adjacent to the first layer. The first layer can be positioned in relation to a wearer of the apparel so that in the event of a breach in the first layer, the second layer is contacted by said fluid. The second layer comprises a bodily fluid detection means that indicates the presence of a specific bodily fluid using an indication for at least one marker chemical for the specific bodily fluid and can include a colorimetric detection means in which the detection means develops a particular color upon exposure to bodily fluid. Other types of detection indication means include compositions that produce odor, temperature variations, swelling, or pressure changes.

The invention may be adapted to detect any bodily fluid including saliva, semen, and blood. In the case of blood, the detection means must include a means by which the presence of blood can be detected. Such blood detection means includes an indicator oxidizable with an accompanying color change when blood is present, a peroxidic substance, and a solid organic acid. A blood detection means of this type is for instance, heme. More particularly, a blood detection means can be achieved by impregnating the second layer with a guaiac reagent of sufficient amount that in combination with a developer and in the presence of blood, the guaiac reaction develops a distinctive color.

In another embodiment of the invention, a bodily fluid protection apparel for alerting a wearer that a breach in the apparel has occurred is disclosed. In this embodiment, a first layer impervious to bodily fluid is supported or overlayed by a second layer, and a liner is included in the apparel, which liner is disposed between the second layer and the wearer. The liner comprises a bodily fluid detection means capable of indicating the presence of bodily fluid. The liner can detect the presence of bodily fluid by a variety of means including colorimetric detection.

The invention can also be adapted to a composite material. The composite material comprises a first layer impervious to bodily fluid. A second layer in the composite material supports the first layer and comprises a bodily fluid detection means which indicates the presence of bodily fluid.

Also disclosed by this invention is a method for indicating that a person has come into contact with at least one specific bodily fluid. The method comprises providing apparel for at least one bodily portion of a wearer, which bodily portion is likely to come into contact with a specific bodily fluid. The apparel comprises a bodily fluid impervious first layer and a second layer adjacent to the first layer. The second layer comprises a bodily fluid detection means for indicating the presence of at least one specific bodily fluid. The bodily fluid detection means can further comprise at least one marker chemical specific for a specific bodily fluid so that the bodily fluid detection means specifically indicates the presence of the specific bodily fluid. The method further comprises the step of having a person wear the apparel with the first layer positioned in relation to the bodily portion so that in the event of a breach in the first layer, the second layer is penetrated by the bodily fluid, thus providing an indication of such penetration whereby the person is made aware of the penetration. The second layer can be placed proximally to the bodily portion of the wearer of the protection apparel.

In any of the foregoing embodiments, the apparel or material can be designed into a variety of forms suitable for a variety of needs. For instance, the apparel or material can be adapted to form gloves, masks, gowns, headdresses, footwear, blankets, or sheets.

BRIEF DESCRIPTION OF THE FIGURES

The above description, as well as further objects, features, and advantages of the present invention, will be more fully understood by reference to the following detailed description of the presently preferred, but nonetheless illustrative, embodiment of the present invention when taken in conjunction with the accompanying drawings, wherein.

DETAILED DESCRIPTION OF THE INVENTION

Figure 1:
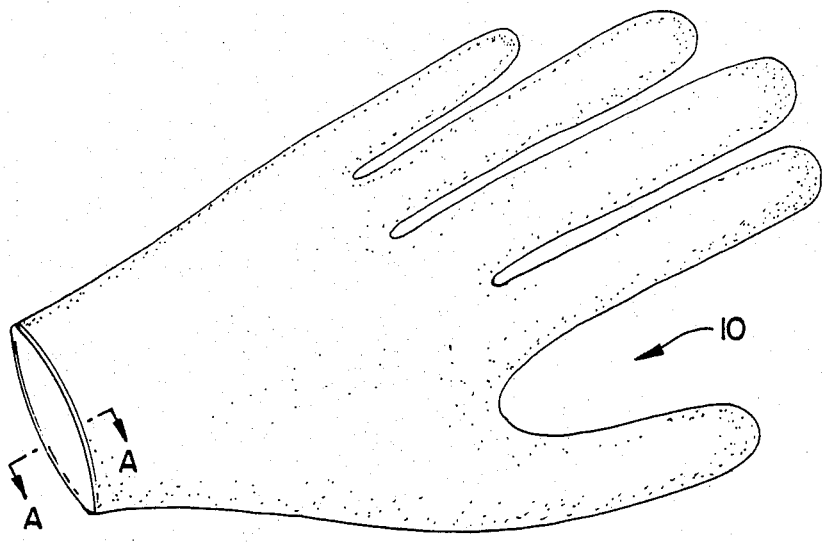
FIG. 1 shows a perspective view of a glove.

The material and protective apparel disclosed herein is designed for any wearer who may come in contact with the bodily fluids of a person suspected of harboring a contagious malady or who seeks protection by means of a barrier from bodily fluids. Individuals who will use the material or wear the protective apparel disclosed by this invention include medical workers of all kinds such as physicians, nurses, dentists, and veterinarians; emergency service personnel such as paramedics, firemen, and policemen; or teachers. The protective material or apparel alerts the wearer to the fact that a bodily fluid, possibly containing the infectious agent from which a wearer is seeking protection, is in imminent danger of or has already come in contact with the wearer. The wearer is alerted to this danger by incorporating in the material or protective apparel a bodily fluid detection means that through a readily discernible mechanism, alerts the wearer that bodily fluid has penetrated the first, fluid impervious layer of the apparel. As will be evidenced below, the invention disclosed herein may be adapted to any apparel including, but not limited to, gloves, footwear, gowns, headdresses, masks, or pants.

The instant invention provides for the detection of a bodily fluid that has passed through, or in another way circumvented, a first, impervious, boundary layer of protective apparel. Detection is accomplished by impregnating or otherwise coating a second layer, which is adjacent or otherwise positioned in relation to the first impervious layer, with a bodily fluid detection means. The impregnation or coating is a composition that is activated by the presence of a bodily fluid. Activation, which is initiated by the presence of bodily fluid, triggers a marker chemical for a specific bodily fluid that alerts the wearer.

A preferred composition for effecting such detection is a composition which is activated by the presence of a bodily fluid to cause a color change. Dyes permitting colorimetric detection, such as for blood, are known in the art. The specific formulations of these compositions vary depending on the fluid to be detected. If more than one bodily fluid is to be detected—for instance, blood and saliva, then the composition contains formulations for detection of more than one bodily fluid.

The detection means used on the second layer of the invention can be adapted to detect any bodily fluid, especially bodily fluids known to transmit or harbor infectious agents. Such bodily fluids include blood, saliva, mucous, and semen.

It will be appreciated that this invention may be adapted to various kinds of apparel depending on both the bodily fluid from which the wearer is seeking protection and the likely mode by which infection is spread. For instance, if the infectious agent from which protection is sought is principally transmitted through airborne particles such as mucoid discharges—for instance, as occurs after a sneeze, then the appropriate apparel may be a mask. If, on the other hand, protection is being sought from blood, then a glove incorporating the two layers of this invention would be appropriate.

The invention can further be used to provide detection of the movement of bodily fluids even when protection from disease is not sought. In one mode, the instant invention can be adapted to be implemented as a birth control device. Most notably, the invention can be adapted as a condom. In this embodiment, if there is a breach in the condom, a detection means would alert the user of the condom and/or the user's sexual partner that a breach in the condom has occurred. With knowledge of such a breach, an individual could take preventive measures that may lessen the chance of pregnancy in view of the breached condom, such as use of a douche. Another advantage that accompanies use of a condom incorporating the instant invention is if the condom user is known to carry a venereal disease or AIDS. In this situation, the sexual partner of the condom wearer can take steps to lessen the chance of infection from the disease as a result of contact with the infectious agent contained in the semen of the condom wearer. In this embodiment an enzyme or other chemical marker, such as hyaluronidase or other chemical principally associated with semen, activates an indicator in the detection means. The presence of semen (and presumptively sperm) can also be achieved using the monosaccharide fructose as a marker chemical. The use of fructose exploits the fact that the presence of fructose is known to be an indicator of the presence of sperm. The mechanism by which this is incorporated into the detection means capitalizes on fructose being a reducing sugar, i.e. a sugar readily oxidized by an alkaline cupric solution. Among the cupric solutions usuable for oxidizing reducing sugars are Benedicts, Haynes, and Barfoeds. For example, a Benedicts solution is applied to the material or apparel of this invention during manufacture. If, while the item is in use, a breach permits semen to come into contact with the fructose comprising detection means, it would react with the Benedicts solution in a colorimetric manner resulting in a visually detectable color change.

Use of this invention in its embodiment as a protection against the spread of infectious disease is deemed extremely significant. Many infectious diseases, including AIDS, are not so highly contagious that a momentary or brief exposure to the infectious agent of the disease results in clinical infection. There is usually a relation between the length of time an individual is exposed to an infectious agent and the probability with which the individual will become infected by the infectious agent. Therefore, if an individual is warned promptly that an exposure to an infectious agent has occurred, the individual can promptly take measures to minimize the length of time he is exposed to the infectious agent. By virtue of the detection means of this invention, a wearer of the protective apparel or material of this invention will be quickly warned that he has been exposed to an infectious agent. This being the case, the wearer can quickly remove the protective apparel and take steps to cleanse himself of the infectious agent. For many diseases, the cleansing steps can be quite simple including merely washing the area exposed to an infectious agent with soap and hot water.

Figure 2:
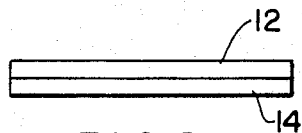
FIG. 2 shows a cross-section along line A—A of a glove having impregnated on the second layer thereof a means for detecting bodily fluid.

Referring now to the drawings, wherein like reference numerals represent like elements, there is shown a glove designated generally by reference numeral 10. As shown in FIG. 2, the glove includes a first or outer layer 12 and a second or inner layer 14. The second layer 14 is adjacent to the first layer 12 and, as shown in FIG. 2, can be a supporting layer. The second layer 14 comprises a detection means including an indicator for at least one marker chemical specific for a particular bodily fluid. Such detection means may be impregnated in or applied to the second layer 14 itself. The first layer 12 is made of a material impervious to bodily fluids. Such materials include, for example, polyvinylchloride, polypropylene, or polyethylene. Preferably, the material used for manufacture of the glove 10 is disposable.

Figure 4:
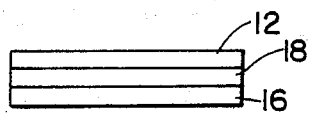
FIG. 4 depicts a cross-section along line A—A having a liner acting as a safety boundary layer in the event of a breach in the glove.
Figure 5:
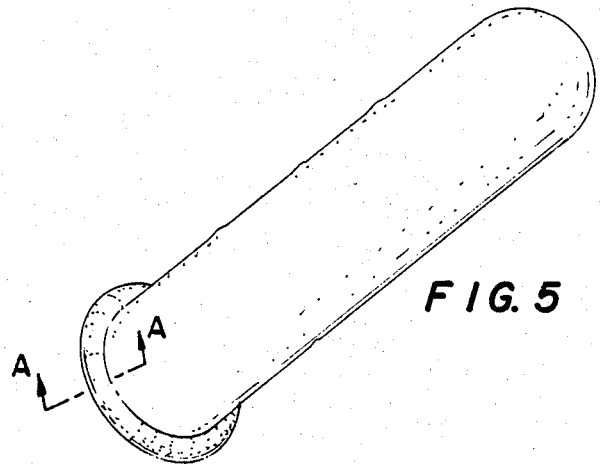
FIG. 5 shows a perspective view of a condom.

Alternatively, as depicted in FIG. 4, the detection means can be incorporated into a separate or third layer or liner 16. Such a liner 16 can be disposed between the wearer and an second layer 18. In this embodiment the second layer 18 does not incorporate the detection means. Rather, the second layer 18 serves to overlay the liner 16 and act as a support for the first layer 12.

Figure 3:
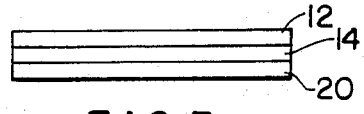
FIG. 3 depicts a cross-section along line A—A having therein a liner impregnated with a bodily fluid detection means.

Regardless of the location of the detection means, this invention can be adapted as shown in FIG. 3. In this embodiment, the wearer is protected by a safety layer 20 disposed between the detection means layer, in FIG. 4 shown as the second layer 14, and the wearer. The safety layer 20 provides an added protection to the wearer. If the first layer 12 of the apparel is breached, triggering the detection means, the wearer is still protected from the specific bodily fluid from which protection is sought. It is thus clear that the safety layer 20 is preferably a liquid impervious layer as exemplified by the various plastic materials suitable for use in the first layer 12.

The detection means layer, whether a second layer 14, a liner 16, or some other form, is made from any of a wide variety of materials capable of being adapted to receive the chemicals of the detection means necessary to indicate a breach in the first layer 12. Suitable materials broadly include cloth, paper, synthetic textiles, and plastics. For example, if cloth or paper is used, the detection means may be impregnated onto the material. Alternatively, if a synthetic or plastic material is used, the detection means may be incorporated into a resin, which is subsequently formed into a fiber or piece of apparel. The material of preference would be dictated by the nature of use for the apparel. For instance, if the apparel were a surgical mask, cloth or paper is preferred. If the apparel were a condom, plastic is preferred.

In the currently preferred embodiment, the detection means alerts the wearer that one or more bodily fluids have somehow penetrated or otherwise breached the first layer 12 by means of developing a color, either where none existed before or by a color change, in the presence of bodily fluid. The detection means used for the instant invention is most preferably a colorimetric detection means, such as a dye. The dye should be nontoxic or, at minimum, substantially nontoxic to avoid sickening the wearer. Preferably, the dye is hypoallergenic to minimize any chance of an adverse reaction by the wearer to the dye. The dye can be applied to the second layer in a variety of known means including, for instance, applying the dye in a dry, particulate state. Among the many dyes deemed acceptable are indigoid, vegetable, and food dyes. In such an embodiment, to facilitate the detection of color by the wearer, it is preferred that the apparel be translucent so that the color is not obscurred or otherwise hidden by the apparel itself.

The detection means can alert the wearer by other than a colorimetric indication of apparel breach. For instance, the apparel could give off an odor indicating that bodily fluids have penetrated the first layer 12. One means by which an odoriferous detection means can be accomplished is through the cleavage of sulfydryl groups causing the creation of the pungent odor associated with hydrogen sulfide. Other types of indication mechanisms that can be employed include a temperature responsive indicator material which produces a warm or cool sensation or a swell-indicating agent which could provide source of pressure on the wearer. A temperature indication means can be achieved using a nontoxic material having a positive or negative heat of solution, to give a heating or cooling effect, respectively. Another type of indication mechanism is a swelling detection means which could be achieved through the use of bibulous cellulosic fibers swelling upon contact with a bodily fluid.

Use of other than a colorimetric alert mechanism with the detection means is especially desirable when the apparel is not readily visible. In these instances, if the detection means undergoes a colorimetric change indicating the presence of a bodily fluid, the wearer would be unaware of such a change because the change would not be seen. Examples of such situations include, for instance, surgery during which a medical worker has his hand inside a torso or any other circumstance in which the wearer's attention is so affixed on another matter that the color change is not readily detected. Also, use of odor or other alternate indication mechanisms as a signal of bodily fluids penetration is advantageous to those wearers who may be color-blind or visually impaired.

As aforementioned, the instant invention is adaptable to detect a variety of bodily fluids. In the case of alerting a wearer to exposure to a bodily fluid possibly containing an infectious agent, the bodily fluids of greatest concern are saliva and blood. If protection is sought from saliva, as may be the case if the wearer is a dentist or dental assistant, then the detection means must alert the wearer to the presence of saliva that has penetrated the first layer 12. In these instances, the apparel would alert the wearer through the incorporation with the detection means of an indicator for a specific chemical marker associated with saliva. Such a chemical marker is amylase. Alternatively, the marker chemical for saliva could be maltose. Maltose is the end product of the reaction between saliva and its enzymatic component amylase, with starch. The dissacharide maltose is a reducing sugar. Therefore, it is readily oxidized by an alkaline cupric solution such as Benedicts, Haynes, or Barfoeds. Use of these solutions, most notably Benedicts, results in a color change when such solutions come into contact and oxidize a reducing sugar. Thus, when saliva comes into contact with the detection means of the invention, the maltose formed from the saliva and starch reaction triggers a colorimetric reaction with an indicator, such an alkaline cupric solution. One skilled in the art will appreciate that any reducing sugar can be adapted to be a marker chemical for this reaction by using an oxidizing agent such as alkaline cupric solution to trigger a detectable change in the apparel of this invention, indicating the presence of the marker material.

If the wearer were seeking protection from blood, the detection means would incorporate chemicals sensitive to blood components, such as, for instance, heme. Compositions for the detection of blood are well known. For instance, most tests for blood in biological specimens exploit the peroxidase or pseudoperoxidase activity of heme derivatives by oxidizing organic compounds used as indicators. The peroxidase substances release, under acidic conditions, hydrogen peroxide or other active oxidants. Acidic components, suitable oxidizable compounds that can form dyes, and typical peroxidic substances are known in the art. Indicator substances oxidizable by the released oxidant then form highly colored reaction products. One indicator reagent that works well is guaiac acid, which, in combination with a developer acting as a reagent to facilitate color formation, forms a color in the presence of blood. Other acceptable reagents include benzidene, ortho-tolidine, ortho-dianisidine, and organic oxides including cumene hydroperoxide and tetramethylbenzedene.

Detection of bodily fluid by this invention is accomplished by a specific bodily fluid coming into contact with an indicator for marker chemical for the specific bodily fluid for which detection is sought. This chemical marker in the detection means triggers the indicator that could be colorimetric, temperature-sensitive, or any other detectable means capable of alerting the wearer of real or potential exposure to bodily fluid. Once alerted, the wearer can quickly change the apparel or material and replace it with apparel or material not breached. Desirably, before replacing the breached apparel or material with new apparel or material, the wearer will take steps to assure that his exposure to the infectious agent is minimized. Such steps could include, as aforediscussed, washing the exposed area with soap and hot water.

It will be understood that the embodiments described herein are merely exemplary and that a person skilled in the art may make many variations and modifications without departing from the spirit and scope of the claimed invention. All such modifications and variations are intended to be included in the scope of the invention, as defined in the appended claims.

What is claimed is:

1. Bodily fluid protection apparel comprising a first layer impervious to blood; and a second layer substantially entirely supporting said first layer, said second layer being adapted to be disposed adjacent to a wearer and comprising substantially throughout the entire said second layer a blood detection means having an indicator for at least one blood specific marker so that said blood detection means indicates the presence of blood whereby said wearer is alerted that a breach in said apparel has occurred that has permitted the introduction of said blood to said second layer.

2. The apparel of claim 1 wherein said blood detection means is a colorimetric detection means which develops a color upon exposure to blood.

3. The apparel of claim 1 wherein said first layer is translucent.

4. The apparel of claim 1 wherein said apparel is a glove.

5. The apparel of claim 1 wherein said blood detection means includes an indicator oxidizable with an accompanying color change in the presence of blood.

6. The apparel of claim 1 wherein said blood detection means includes a peroxidic substance, a solid organic acid, and an indicator oxidizable with an accompanying color change in the presence of blood.

7. The apparel of claim 1 wherein said blood detection means develops a color upon exposure to heme.

8. The apparel of claim 1 wherein said second layer is impregnated with a guaiac reagent of sufficient amount that in combination with a developer and in the presence of blood, said guaiac reagent develops a distinctive color.

9. The protection apparel of claim 1 wherein said second layer further comprises a blood absorbing means for absorbing blood.

10. The bodily fluid protection apparel of claim 1 wherein said apparel is a condom.

11. Bodily fluid protection apparel comprising
a first layer impervious to bodily fluid;
a second layer supporting said first layer; and
a liner disposed between said second layer and a wearer, said liner comprising bodily fluid detection means having an indicator for at least one marker chemical for a specific bodily fluid so that said bodily fluid detection means indicates the presence of said specific bodily fluid, whereby a wearer of said apparel is alerted that a breach in the apparel has occurred which has permitted the introduction of said specific bodily fluid into said liner.

12. The apparel of claim 11 wherein said detection means is a colorimetric detection means which develops a distinctive color upon exposure to bodily fluid.

13. The apparel of claim 11 wherein said apparel is a glove.

14. The apparel of claim 11 wherein said specific bodily fluid is blood, and said marker chemical is a blood marker chemical.

15. The apparel of claim 11 wherein said specific bodily fluid is saliva, and said marker chemical is a saliva marker chemical.

16. The apparel of claim 11 wherein said apparel is a condom.

17. The apparel of claim 16 wherein said specific bodily fluid detected is semen and wherein said liner comprising said bodily fluid detection means comprises at least one marker chemical for detecting semen.

18. The apparel of claim 17 wherein said marker chemical can detect hyaluronidase.

19. Bodily fluid protection apparel comprising a first layer impervious to bodily fluids; a second layer impervious to bodily fluids; and a third layer disposed between said first layer and said second layer comprising bodily fluid detection means having an indicator for at least one marker chemical for a specific bodily fluid so that said bodily fluid detection means indicates the presence of said bodily fluid, whereby an individual is alerted that a breach in at least one of said first and second layers has occurred which has permitted introduction of said specific bodily fluid into said second layer.

20. The bodily fluid protection apparel of claim 19 wherein said third layer comprises a marker chemical for detecting semen.

21. The bodily fluid protection apparel of claim 20 wherein said third layer further comprises a marker chemical for detecting saliva.

22. The bodily fluid protection apparel of claim 20 wherein said third layer further comprises a marker chemical for detecting blood.

23. A condom having a first layer impervious to bodily fluid and a second layer adjacent to said first layer, said second layer comprising bodily fluid detection means having an indicator for at least one marker chemical for semen so that said bodily fluid detection means indicates the presence of said semen, whereby an individual is alerted that a breach in the condom has occurred which has permitted the introduction of said semen into said second layer.

24. Bodily fluid protection apparel comprising a first layer impervious to blood, a second layer substantially entirely supporting said first layer, and a blood detection means selected between said first and said second layers, said blood detection means having an indicator for at least one blood specific marker so that said blood detection means indicates the presence of blood wherby said wearer is alerted that a breach in said apparel has occured that has permitted the introducntion of said blood to said blood detection means.

25. The fluid protection apparel of claim 24 wherein said apparel is a glove.

26. Bodily fluid protection apparel comprising a first layer impervious to saliva; and a second layer substantially entirely supporting said first layer, said second layer being adapted to be disposed adjacent to a wearer and comprising substantially throughout the entire said second layer a saliva detection means having an indicator for at least one saliva specific marker so that said saliva detection means indicates the presence of saliva whereby said wearer is alerted that a breach in said apparel has occured that has permitted the introduction of said saliva to said second layer.

27. The apparel of claim 26 wherein said second layer further comprises a blood detection means.

28. The apparel of claim 26 wherein said saliva marker chemical detects the presence of amylase.

29. Bodily fluid protection apparel comprising a first layer impervious to semen; and a second layer substantially entirely supporting said first layer, said second layer being adapted to be disposed adjacent to a wearer and comprising substantially throughout the entire said second layer a semen detection means having an indicator for at least one semen specific marker so that said semen detection means indicates the presence of semen whereby said wearer is alerted that a breach in said apparel has occured that has permitted the introduction of said semen to said second layer.

30. The bodily fluid protection apparel of claim 28 wherein said specific bodily fluid detected by said bodily fluid, detection means is a bodily fluid comprising hyaluronidase.

* * * * *